(12) United States Patent
Scott et al.

(10) Patent No.: US 11,248,237 B2
(45) Date of Patent: Feb. 15, 2022

(54) GENETICALLY ENGINEERED LARVAE FOR WOUND HEALING

(71) Applicant: North Carolina State University, Raleigh, NC (US)

(72) Inventors: Maxwell J. Scott, Apex, NC (US); Rebecca J. Davis, Raleigh, NC (US); Esther J. Belikoff, Apex, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 845 days.

(21) Appl. No.: 15/923,595

(22) Filed: Mar. 16, 2018

(65) Prior Publication Data

US 2018/0265892 A1 Sep. 20, 2018

Related U.S. Application Data

(60) Provisional application No. 62/473,704, filed on Mar. 20, 2017.

(51) Int. Cl.
| | |
|---|---|
| *C12N 15/85* | (2006.01) |
| *C07K 14/435* | (2006.01) |
| *C07K 14/49* | (2006.01) |
| *A61K 35/64* | (2015.01) |
| *A61K 38/18* | (2006.01) |
| *A01K 67/033* | (2006.01) |

(52) U.S. Cl.
CPC ...... *C12N 15/8509* (2013.01); *A01K 67/0339* (2013.01); *A61K 35/64* (2013.01); *A61K 38/1858* (2013.01); *C07K 14/43577* (2013.01); *C07K 14/49* (2013.01); *A01K 2217/072* (2013.01); *A01K 2227/706* (2013.01); *A01K 2267/02* (2013.01); *C12N 2015/8518* (2013.01); *C12N 2830/00* (2013.01)

(58) Field of Classification Search
None
See application file for complete search history.

(56) References Cited

U.S. PATENT DOCUMENTS

2019/0320655 A1* 10/2019 Swale .................... A01N 43/40

OTHER PUBLICATIONS

Ali RA, Mellenthin K, Fahmy K, Da Rocha S, Baumgartner S. Structural conservation of the salivary gland-specific slalom gene in the blowfly Lucilia sericata. Dev Genes Evol. 2005;215(10):537-43.
Altincicek B, Vilcinskas A. Septic injury-inducible genes in medicinal maggots of the green blow fly Lucilia sericata. Insect Mol Biol. 2009;18(1):119-25.
Cazander G, Pritchard DI, Nigam Y, Jung W, Nibbering PH. Multiple actions of Lucilia sericata larvae in hard-to-heal wounds: larval secretions contain molecules that accelerate wound healing, reduce chronic inflammation and inhibit bacterial infection. Bioessays. 2013;35(12):1083-92.
Concha C, Belikoff EJ, Carey BL, Li F, Schiemann AH, Scott MJ. Efficient germ-line transformation of the economically important pest species Lucilia cuprina and Lucilia sericata (Diptera, Calliphoridae). Insect Biochem Mol Biol. 2011;41(1):70-5.
Concha C, Edman RM, Belikoff EJ, Schiemann AH, Carey B, Scott MJ. Organization and expression of the Australian sheep blowfly (Lucilia cuprina) hsp23, hsp24, hsp70 and hsp83 genes. Insect Mol Biol. 2012;21(2):169-80.
Jaklic D, Lapanje A, Zupancic K, Smrke D, Gunde-Cimerman N. Selective antimicrobial activity of maggots against pathogenic bacteria. J Med Microbiol. 2008;57(Pt 5):617-25.
Kawabata T, Mitsui H, Yokota K, Ishino K, Oguma K, Sano S. Induction of antibacterial activity in larvae of the blowfly Lucilia sericata by an infected environment. Med Vet Entomol. 2010;24(4):375-81.
Li X, Heinrich JC, Scott MJ. piggyBac-mediated transposition in Drosophila melanogaster: an evaluation of the use of constitutive promoters to control transposase gene expression. Insect Mol Biol. 2001;10:447-55.
Li F, Vensko SP, 2nd, Belikoff EJ, Scott MJ. Conservation and Sex-Specific Splicing of the transformer Gene in the Calliphorids Cochliomyia hominivorax, Cochliomyia macellaria and Lucilia sericata. PLoS One. 2013;8(2):e56303.
Li F, Wantuch HA, Linger RJ, Belikoff EJ, Scott MJ. Transgenic sexing system for genetic control of the Australian sheep blow fly Lucilia cuprina. Insect Biochem Mol Biol. 2014;51:80-8.
Lobo N, Li X, Fraser MJ, Jr. Transposition of the piggyBac element in embryos of Drosophila melanogaster, Aedes aegypti and Trichoplusia ni. Mol Gen Genet. 1999;261(4-5):803-10.
Scott MJ. Development and evaluation of male-only strains of the Australian sheep blowfly, Lucilia cuprina. BMC Genet. 2014;15 Suppl 2:S3.
Sze SH, Dunham JP, Carey B, Chang PL, Li F, Edman RM et al. A de novo transcriptome assembly of Lucilia sericata (Diptera: Calliphoridae) with predicted alternative splices, single nucleotide polymorphisms and transcript expression estimates. Insect Mol Biol. 2012;21(2):205-21.
Thomas S, Andrews AM, Hay NP, Bourgoise S. The anti-microbial activity of maggot secretions: results of a preliminary study. J Tissue Viability. 1999;9(4):127-32.
Cerovsky V, Zdarek J, Fucik V, Monincova L, Voburka Z, Bem R. Lucifensin, the long-sought antimicrobial factor of medicinal maggots of the blowfly Lucilia sericata. Cell Mol Life Sci. 2010;67(3):455-66.
Chan DC, Fong DH, Leung JY, Patil NG, Leung GK. Maggot debridement therapy in chronic wound care. Hong Kong Med J. 2007;13(5):382-6.

(Continued)

*Primary Examiner* — James D Schultz
(74) *Attorney, Agent, or Firm* — Myers Bigel, P.A.

(57) ABSTRACT

The present invention relates to methods and compositions for maggot debridement therapy. More specifically, the invention relates to recombinant nucleic acid constructs, transgenic maggots comprising the recombinant nucleic acids, methods for making the maggots, and methods for the use of the maggots, including debridement and promoting of wound healing.

18 Claims, 5 Drawing Sheets

Specification includes a Sequence Listing.

(56) References Cited

OTHER PUBLICATIONS

Linger, RJ et al. Towards next generation maggot debridement therapy: transgenic Lucilia sericata larvae that produce and secrete a human growth factor. BMC Biotechnology. 2016;16:30, 12 pages.
Huberman L, Gollop N, Mumcuoglu KY, Block C, Galun R. Antibacterial properties of whole body extracts and haemolymph of Lucilia sericata maggots. J Wound Care. 2007:16(3): 123-7.

* cited by examiner

Fig. 2
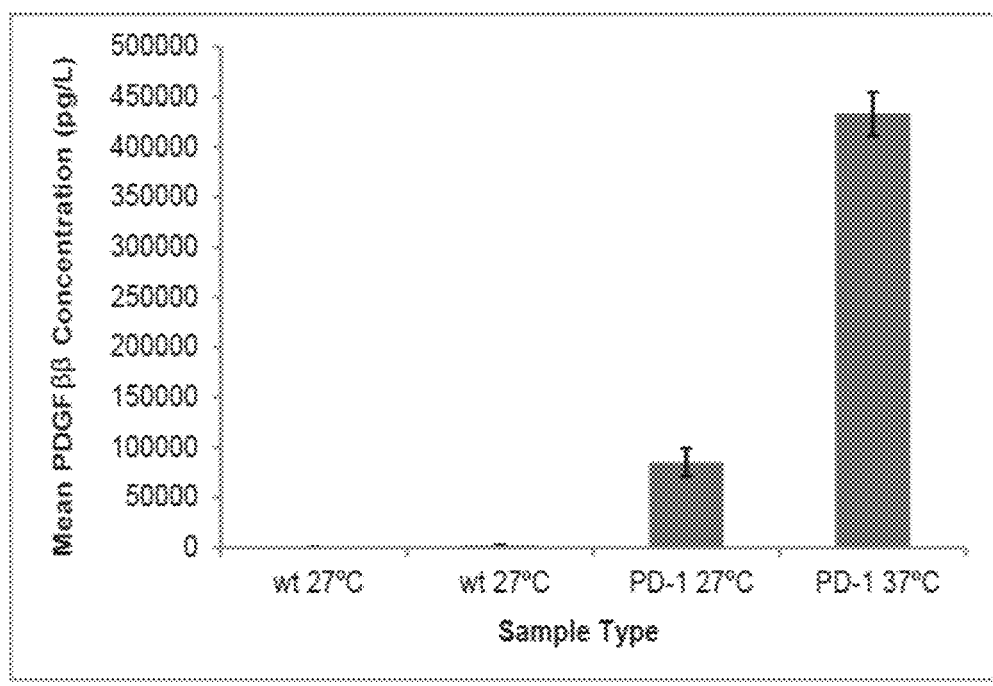
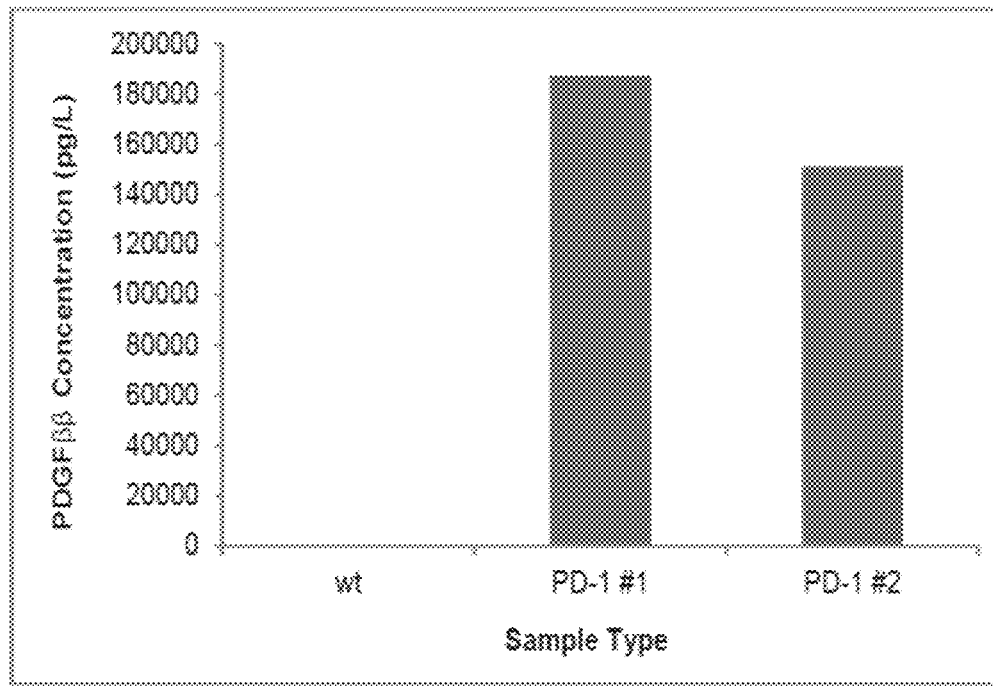

Fig. 4
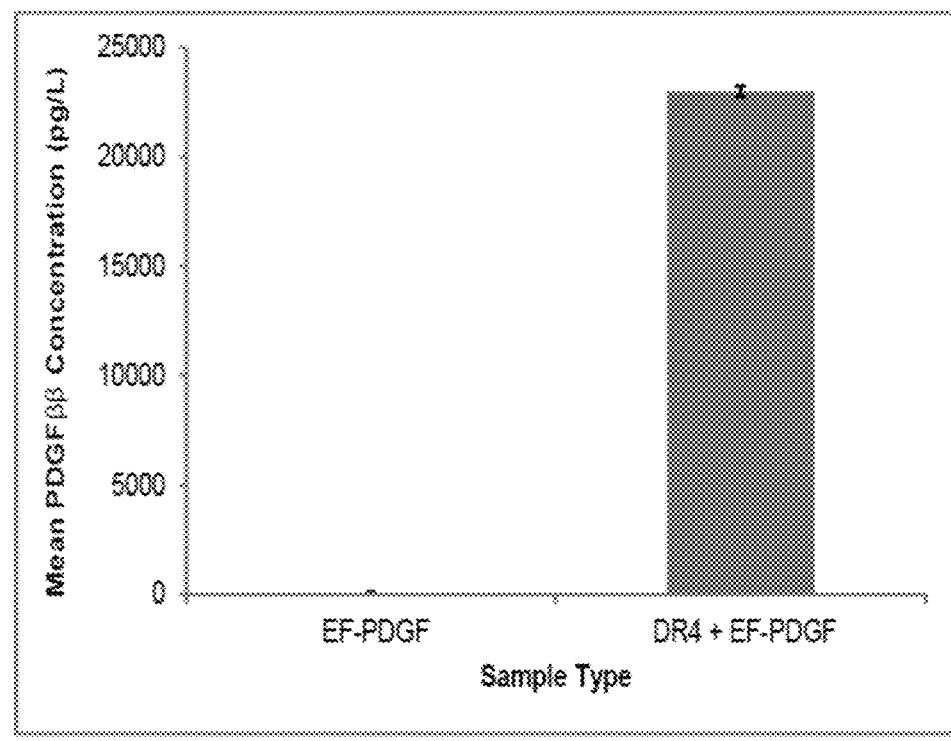
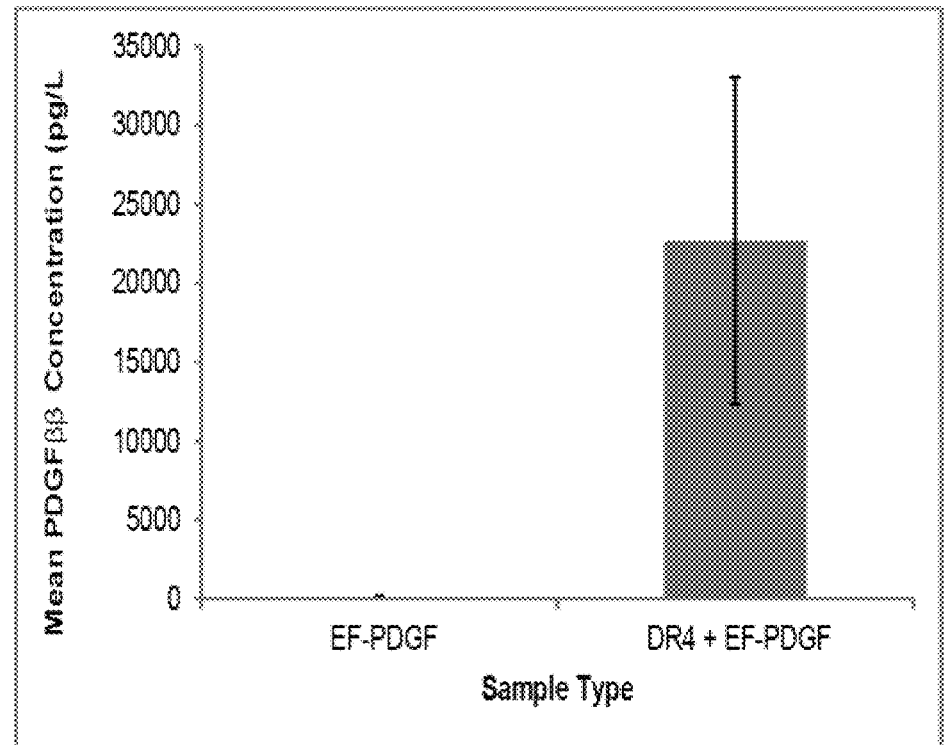

SEQUENCE LISTING

```
<160> NUMBER OF SEQ ID NOS: 21

<210> SEQ ID NO 1
<211> LENGTH: 20
<212> TYPE: PRT
<213> ORGANISM: Lucilia sericata

<400> SEQUENCE: 1

Met Lys Ser Phe Leu Leu Val Leu Phe Ala Phe Leu Ala Val Phe Ala
1               5                   10                  15

Phe Val Gln Ala
            20

<210> SEQ ID NO 2
<211> LENGTH: 87
<212> TYPE: PRT
<213> ORGANISM: Lucilia sericata

<400> SEQUENCE: 2

Met Lys Ser Phe Leu Leu Val Leu Phe Ala Phe Leu Ala Val Phe Ala
1               5                   10                  15

Phe Val Gln Ala Asp Asp Cys Lys Ile Asp Gly His Val Val Lys Val
            20                  25                  30

Gly Glu Thr Tyr Ser Leu Pro Gly Lys Cys Ser Glu Ile Lys Cys Asn
        35                  40                  45

Gly Pro Asp Ser Phe Thr Ala Lys Thr Cys Pro Glu Gln Ser Leu
    50                  55                  60

Lys Thr Cys Lys Leu Ile Pro Gln Asp Asn Thr Lys Pro Phe Pro Glu
```

-continued

```
                65                  70                  75                  80
Cys Cys Pro Arg His Glu Cys
                85

<210> SEQ ID NO 3
<211> LENGTH: 43
<212> TYPE: DNA
<213> ORGANISM: Lucilia cuprina

<400> SEQUENCE: 3
gagctcctcg agtagggtgg gcaattttt ctaatgccca tta                        43

<210> SEQ ID NO 4
<211> LENGTH: 36
<212> TYPE: DNA
<213> ORGANISM: Lucilia cuprina

<400> SEQUENCE: 4
ggatcctgga taggcttcac ggtccagttc atcgat                               36

<210> SEQ ID NO 5
<211> LENGTH: 27
<212> TYPE: DNA
<213> ORGANISM: Lucilia cuprina

<400> SEQUENCE: 5
aagcttagtc aatctcaatt tcattcc                                         27

<210> SEQ ID NO 6
<211> LENGTH: 31
<212> TYPE: DNA
<213> ORGANISM: Lucilia cuprina

<400> SEQUENCE: 6
gcggccgcct cgagaatgat atacaagg a                                      31

<210> SEQ ID NO 7
<211> LENGTH: 33
<212> TYPE: DNA
<213> ORGANISM: Lucilia cuprina

<400> SEQUENCE: 7
attatcatta tctactagtt cagttctagt tac                                  33

<210> SEQ ID NO 8
<211> LENGTH: 33
<212> TYPE: DNA
<213> ORGANISM: Lucilia cuprina

<400> SEQUENCE: 8
attatcggat ccctctttgg ttttcttaaa acg                                  33

<210> SEQ ID NO 9
<211> LENGTH: 29
<212> TYPE: DNA
<213> ORGANISM: Lucilia cuprina

<400> SEQUENCE: 9
ttatcatgaa gtcgttcttg ttggtgttg                                       29

<210> SEQ ID NO 10
<211> LENGTH: 30
<212> TYPE: DNA
```

<210> SEQ ID NO 10
<211> LENGTH: 30
<212> TYPE: DNA
<213> ORGANISM: Lucilia cuprina

<400> SEQUENCE: 10
tgaaagctta ggtcacggga cgggcggcag                            30

<210> SEQ ID NO 11
<211> LENGTH: 39
<212> TYPE: DNA
<213> ORGANISM: Cochliomyia hominivorax

<400> SEQUENCE: 11
caattcacgc aagaaaatct ctttgttgga atagaaggt                  39

<210> SEQ ID NO 12
<211> LENGTH: 46
<212> TYPE: DNA
<213> ORGANISM: Cochliomyia hominivorax

<400> SEQUENCE: 12
gatcaaccac aatctaatat attataactt ttttcacttt tcagtt          46

<210> SEQ ID NO 13
<211> LENGTH: 35
<212> TYPE: DNA
<213> ORGANISM: Cochliomyia hominivorax

<400> SEQUENCE: 13
ttgtcttttc gctcgcttgg aaactctcga tgtat                      35

<210> SEQ ID NO 14
<211> LENGTH: 46
<212> TYPE: DNA
<213> ORGANISM: Cochliomyia hominivorax

<400> SEQUENCE: 14
atagcggccg ctgtcattac tagagtttaa gttataacaa ttgtat          46

<210> SEQ ID NO 15
<211> LENGTH: 47
<212> TYPE: DNA
<213> ORGANISM: Cochliomyia hominivorax

<400> SEQUENCE: 15
acgctgcaga tctggaaata caataggaaa ataaagtta gcgaatt          47

<210> SEQ ID NO 16
<211> LENGTH: 42
<212> TYPE: DNA
<213> ORGANISM: Homo sapiens

<400> SEQUENCE: 16
atgaagtcgt tcttgttggt gttgttcgcc ttcttggccg tt              42

<210> SEQ ID NO 17
<211> LENGTH: 45
<212> TYPE: DNA
<213> ORGANISM: Homo sapiens

<400> SEQUENCE: 17
ccggagttta aaccctaggc gcgccatgag ctcaagcttt catta           45

<210> SEQ ID NO 18
<211> LENGTH: 25

```
<212> TYPE: DNA
<213> ORGANISM: Homo sapiens

<400> SEQUENCE: 18
gaaattgtgc gtaaaaagcc cattt                                              25

<210> SEQ ID NO 19
<211> LENGTH: 25
<212> TYPE: DNA
<213> ORGANISM: Homo sapiens

<400> SEQUENCE: 19
aacagtttca catttacagg ccaaa                                              25

<210> SEQ ID NO 20
<211> LENGTH: 24
<212> TYPE: DNA
<213> ORGANISM: Lucilia cuprina

<400> SEQUENCE: 20
accactgttc acacgaaacc cttc                                               24

<210> SEQ ID NO 21
<211> LENGTH: 27
<212> TYPE: DNA
<213> ORGANISM: Lucilia cuprina

<400> SEQUENCE: 21
atctcggttg gattttaaac tttgaaa                                            27
```

GENETICALLY ENGINEERED LARVAE FOR WOUND HEALING

STATEMENT OF PRIORITY

This application claims the benefit, under 35 U.S.C. § 119(e), of U.S. Provisional Application No. 62/473,704 was filed on Mar. 20, 2017, the entire contents of which is incorporated by reference herein.

STATEMENT REGARDING ELECTRONIC FILING OF A SEQUENCE LISTING

A Sequence Listing in ASCII text format, submitted under 37 C.F.R. § 1.821, entitled 5051-916 ST25.txt, 4,284 bytes in size, generated Mar. 16, 2018 and filed via EFS-Web, is provided in lieu of a paper copy. This Sequence Listing is hereby incorporated herein by reference into the specification for its disclosures.

FIELD OF THE INVENTION

The present invention relates to methods and compositions for wound healing, in particular, the invention relates to maggot debridement therapy.

BACKGROUND

Diabetes is a global health care issue. Three hundred-eighty-two million people were reported to have diabetes in 2013 [1]. Additionally, the estimated cost of diabetic foot ulcers to the American health care system was estimated to be $9-13 billion in addition to care for diabetes in 2013 [2]. Maggot debridement therapy (MDT) is a cost-effective, FDA-approved treatment for diabetic foot ulcers [3, 4]. MDT commonly involves the application of sterile *Lucilia sericata* larvae to a non-healing wound to promote healing and decrease infection. MDT has been applied successfully in more than 20 additional medical conditions [5, 6]. MDT promotes healing in part through digestion and mechanical removal of necrotic tissue. Debridement is a critical component of effective wound healing [5, 7]. Enzyme application and mechanical debridement have been studied in clinical trials, but challenges such as expense and potential damage to healthy tissue stunt the large-scale effectiveness of these treatment options [8]. In contrast, larvae leave behind healthy tissue. Larvae have been shown to ingest fluorescent bacteria in vitro [9] as well as raise the pH of the wound environment via excretions and secretions (ES), which results in inhibition of bacterial growth [10]. Further, studies have identified a number of specific factors and fractions within excretions/secretions that exhibit antibacterial activity in vitro [11]. For example, the insect defensin homologue lucifensin was detected in the gut and salivary glands of *L. sericata* larvae and identified in wound washings from MDT patients [12]. Lucifensin exhibited antibacterial activity against a panel of Gram positive bacteria [12, 13]. Some data suggests expression and secretion of antibacterial factors by larvae is not constitutive, but induced by the wound environment [14-16]. The antibacterial mechanisms of MDT are free from the limitations of antibiotic resistance frequently seen in the clinic. Indeed, maggot debridement therapy has been shown to be effective in treatment of methicillin resistant *Staphylococcus aureus* (MRSA) in vitro as well as in clinical case studies [17].

It is clear from these studies that larvae significantly alter the wound environment during MDT. Maggot ES may also alter the local inflammatory response. For example, *L. sericata* excretions/secretions modulate neutrophil migration and adhesion and alter expression of pattern recognition receptor levels [18]. Excretions/secretions also increased the secretion of anti-inflammatory cytokine IL-10, while inhibiting secretion of pro-inflammatory cytokines TNF-alpha and IL-12p40 [19].

In addition to the impact of MDT on the immune response in the wound, MDT also promotes wound healing through formation of granulation tissue [20, 21]. Previous studies have confirmed that increased growth factor levels in the wound environment may contribute to more effective healing. Increased Hepatocyte Growth Factor (HGF) levels were measured in femoral vein blood of patient during MDT and higher levels of HGF mRNA and protein were measured in 3T3 cells treated with excretions/secretions [22]. Further, it has been shown that maggot extracts stimulate fibroblast proliferation in culture [23].

BRIEF DESCRIPTION OF THE DRAWINGS

FIG. 2—PDGF-B protein is inducible in transgenic PD-1 *L. sericata* lysate and hemolymph. A. Mean PDGF-B concentration in wild type (wt) and PD-1 whole larval lysate under control and heat shock conditions. B. PDGF-B concentration in pooled wt or PD-1 adult hemolymph samples after heat shock.

FIG. 4—PDGF-B protein is detectable in larval lysate and excretions/secretions (ES) of larvae that carry both tTA driver (DR4) and tTA-regulated pdgf-b (EF-PDGF) transgenes. A. Mean PDGF-B concentration in control effector-alone and tTA-driver plus effector larvae. B. Mean PDGF-B concentration in effector-alone and tTA-driver plus effector larval ES.

DESCRIPTION

Figure 1:
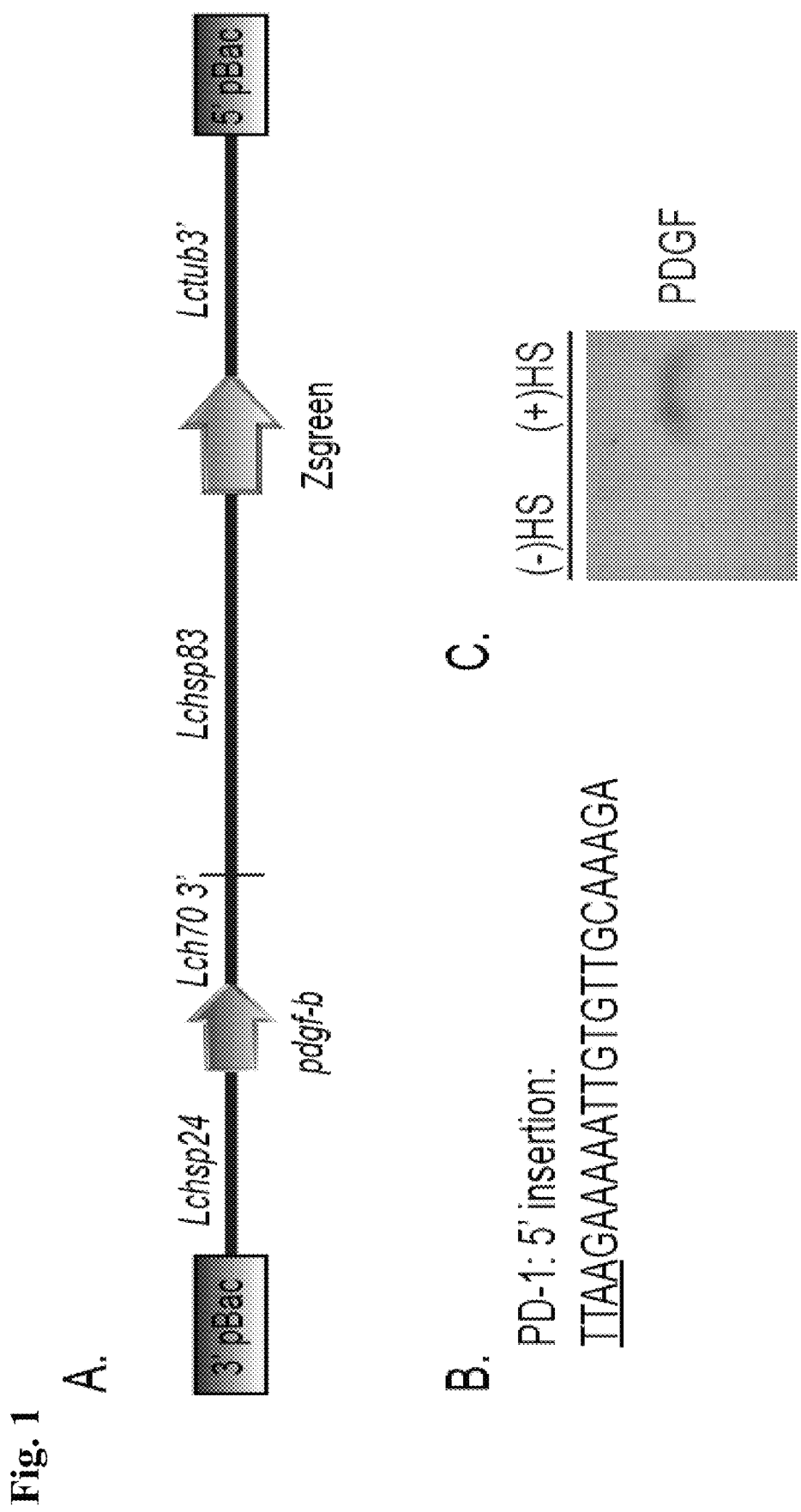
FIG. 1—Heat inducible expression of Platelet-Derived Growth Factor Beta (pdgf-b) mRNA in transgenic PD-1 *L. sericata*. A. Schematic of heat-inducible PDGF-B gene construct in a piggyBac transformation vector with a ZsGreen marker gene. B. Genomic DNA sequence adjacent to the 5' pBac end in the PD-1 transgenic line. The TTAA insertion site is underlined. C. RT-PCR amplification of pdgf-b on total RNA obtained from first instar PD-1 larvae that had been given a heat shock (+HS) or no heat shock (−HS).

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount.

The role of human platelet-derived growth factor (PDGF) in wound healing is well established [24]. PDGF is a cationic hetero or homo-dimer consisting of a combination of alpha and beta subunit chains containing multiple intra- and inter-chain disulfide bonds. The subunits are produced in a pro form by endothelial cells, fibroblasts, immune system cells, and others, and are cleaved to a mature form which interacts with the extra-cellular matrix (ECM) and cell surface PDGF receptors. Via activation of the PDGF receptor and subsequently PI3 kinase and mitogen-activated protein kinase (MAPK), PDGF stimulates cell survival, fibroblast proliferation and chemotaxis, actin reorganization, and production and secretion of other growth factors, ECM constituents, and metalloproteases [24]. Because of the extensive role of PDGF in wound healing, clinical trials have been done investigating the utility of a topical gel containing recombinant human PDGF-BB produced in *Escherichia coli* (Becaplermin) [25]. Immunostaining of wounds treated with PDGF-BB showed increased fibroblasts, increased collagen fibril formation, and healing (as measured by decreased wound size) [26]. Overall, however, studies testing the topical gel have seen limited success [27-31].

Decreased growth factor secretion has been observed in macrophages isolated from a diabetic mouse model [32]. Interestingly, the proliferative response of chronic wound fibroblasts to growth factors and cytokines, including PDGF, may be reduced as well [33]. These findings correlate with an inconsistent response to topical growth factor treatment [34, 29] and indicate the need for therapies combining multiple mechanisms to promote healing.

There is great potential for improving the efficacy of maggot debridement therapy (MDT). The benefits of larval wound debridement could be combined with more potent mechanisms of wound healing and bacterial inhibition. Genetically modified larvae engineered to secrete tailored human growth factors or antibacterial peptides effective against Gram positive and Gram negative bacteria could have the potential to synergistically improve wound healing and result in shorter hospital stays and reduced costs for providers, caregivers and patients. Here, we present a novel concept in MDT technology that combines the established benefits of MDT with the power of genetic engineering to promote healing. The focus of this study is to create and characterize transgenic *L. sericata* larvae that express growth factors (e.g., hPDGF (Human Platelet-Derived Growth Factor)) and/or antimicrobial peptides at detectable levels in ES with potential for clinical utility in wound healing.

In some embodiments, a transgenic maggot of the invention may comprise, two recombinant nucleic acid constructs, a "driver construct" (a recombinant nucleic acid construct encoding a transcription factor) and an "effector construct" (a recombinant nucleic acid construct encoding at least one antimicrobial peptide and/or a mammalian growth factor), wherein the maggot may thereby secrete and/or excrete growth factors and/or antimicrobial peptides to enhance maggot debridement therapy (MDT) and to improve wound healing. In some embodiments, a transgenic maggot of the invention may comprise a driver construct (recombinant nucleic acid construct encoding at least one antimicrobial peptide and/or a mammalian growth factor) but not an effector construct, wherein the maggot may thereby secrete and/or excrete human growth factors and/or antimicrobial peptides to enhance maggot debridement therapy (MDT) and to improve wound healing. In some embodiments, the transgenic maggots of the invention may be made using a "vector." In some embodiments, the transgenic maggots of the invention may be identified using a fluorescent protein "marker" gene.

As used herein, a "driver construct" refers to a recombinant nucleic acid construct of the invention. In some embodiments, a driver construct may comprise a promoter driving expression of a transcription factor.

Any promoter functional in an insect may be used with the recombinant nucleic acid molecules of the invention. Example promoters may include but are not limited to, constitutive (e.g. hsp83 (heat shock protein 83), ubiquitin), salivary-gland specific (e.g. slalom) or Malpighian tubule-specific. Proteins are secreted from the larval salivary gland and excreted from the Malpighian tubules of maggots. Since maggot secretion/excretions play important roles in MDT, in some embodiments, transcription factor expression may be directed to those tissues. Thus, in some embodiments, $L.$ $sericata$ promoters active in the salivary gland and/or Malpighian tubules will be operably linked to the transcription factors to be expressed.

Transcription factors useful with the invention include but are not limited to, tetracycline transactivator (tTA), GAL4, erythromycin transactivator (ET), vanillic acid transactivator (Van1). tTA is repressed by tetracycline, ET by erythromycin and Van1 by vanillic acid, a food additive. In some embodiments, such conditional systems may be used to control expression of antimicrobial factors or growth factors, which may be used to minimize any deleterious effects that the antimicrobial factors or growth factors may have on the viability of the maggots.

As used herein, an "effector construct" refers to a recombinant nucleic acid construct of the invention. In some embodiments, an "effector construct" may comprise an enhancer-promoter construct driving expression of, for example, one or more antimicrobial peptides and/or mammalian growth factors.

In some embodiments an enhancer comprises of multiple copies (e.g., two or more (2, 3, 4, 5, 6, 7, 8, 9, 10, or more)) of the binding site of the transcription factor. Example binding sites include but are not limited to tet operator (tetO) for tTA, upstream activating sequence (UAS) for GAL4, MphR(A)-specific operator from $E.$ $coli$ (ETR) for ET and the VanO operator from $C.$ $crescentus$ for Van1. A promoter useful with the effector construct may be a core or minimal promoter required for gene transcription. In some embodiments, alone the core operator has very little activity. Thus, in some embodiments, expression is largely dependent upon the transcription factor binding to the enhancer. Examples of core promoters may be from $L.$ $cuprina$. In some embodiments, a core promoter is typically from −40 to +30 bp of the gene (about 70 bp). In some embodiments, a core promoter can include, but is not limited to the core promoter from an hsp70 gene, a P element or a Pgd gene or a synthetic sequence based on known functional core promoters. In some embodiments, the hsp70 gene may be from $Lucilia$ $cuprina$ or from $Drosophila$ $melanogaster$. In some embodiments, the P element or a Pgd gene may be from $Drosophila$ $melanogaster.$ The one or more mammalian growth factors that may be encoded in constructs of the invention and/or may be excreted or secreted by maggots of the invention that may enhance wound healing include, but are not limited to, platelet derived growth factor B (PDGF-B), fibroblast growth factors 1 and 2 (FGF1, FGF2), hepatocyte growth factor (HGF), keratinocyte growth factor (KGF), granulocyte macrophage colony-stimulating factor (GM-CSF) and epidermal growth factor (EGF), which have been shown to play important roles in wound healing. Recombinant PDGF-B (made in $E.$ $coli$) is approved for topical application to wounds. In some embodiments, a growth factor useful with the invention may be PDGF-B, FGF1 and/or FGF2

In some embodiments, the polynucleotides encoding the one or more antimicrobial peptides and/or mammalian growth factors may be operably linked to a polynucleotide encoding an amino-terminal signal peptide that functions in insect cells. The signal peptides may facilitate secretion from insect cells. Example signal peptides include but are not limited to the peptide MKSFLLVLFAFLAVFAFVQA (SEQ ID NO:1) (Linger et al. BMC Biotechnol. 16:30 (2016) pages 1-12) or the signal sequence from the 87 amino acid venom peptide (p300) identified in $Lucilia$ $sericata$ salivary gland (MKSFLLVLFAFLAVFA FVQADDCK-IDGHVVKVGETYSLPGKC-SEIKCNGPDSFTAKTCPPEQSLKTCKLIPQDN TKPFPECCPRHEC) (SEQ ID NO:2) (Sze et al. Insect Mol. Biol. 21(2):205-221(2012).

In some embodiments, the one or more antimicrobial peptides encoded on the constructs of the invention may be active against gram positive bacteria (e.g., Lucifensin). In some embodiments, the one or more antimicrobial peptides encoded on the constructs of the invention may be active against gram negative bacteria (e.g., cecropin B) or both (e.g., moricin). Insect peptides may be expressed as pre-pro proteins that are processed in insect cells before secretion. Thus, in some embodiments, they will not need an additional signal peptide. Example antimicrobial peptides useful with the invention include, but are not limited to, cecropin B, Lucifensin, and/or moricin (from, e.g., $Bombyx$ $mori$).

In some embodiments, the recombinant nucleic acid constructs may be comprised in transformation vectors. Any transformation vector useful in insect transformation may be used with the constructs of the present invention. In some embodiments, transformation vectors used for making transgenic insects may be based on transposable elements. For example, the vector may be based on the piggyBac element. The vectors may comprise the 5' and 3' ends of the transposon that are sufficient for mobilization in the presence of transposase (supplied from another plasmid or by co-injecting insect embryos with RNA that encodes the transposase). Additional example vectors useful with the present invention include, but are not limited to, vectors based on the Minos transposon and the Mos1 element.

In some embodiments, fluorescent protein markers may be used with the recombinant nucleic acid constructs of the invention. In some embodiments, a fluorescent protein marker may include, but is not limited to, ZsGreen, DsRed-express 2, tdTomato, AmCyan and/or TagBFP. In some embodiments, the fluorescent protein markers may be codon optimized for expression in a species of maggot of interest. Additional examples of fluorescent protein markers, include, but are not limited to, EGFP (enhanced GFP (green fluorescent protein)) and it's derivatives EYFP(enhanced YFP (yellowish-green fluorescent protein)) and ECFP (enhanced CFP (cyan fluorescent protein)). Further example fluorescent protein markers include, but are not limited to, Venus (bright yellow), mCherry, and/or mCitrine. In some embodiments, expression of fluorescent proteins may be driven by a strong constitutive (e.g., Lchsp83 promoter). In some embodiments, a strong tissue-specific promoter active in maggots may be used. In some embodimetns, the use of a strong tissue-specific promoter may facilitate multiplexing effectors.

In some embodiments, blow fly species useful with the invention include, but are not limited to, *Lucilia sericata* (also known as *Phaenicia sericata*) and/or *Protophormia terraenovae*.

As used herein, "promoter" refers to a nucleotide sequence, usually upstream (5') to its coding sequence, which controls the expression of the coding sequence by providing the recognition for RNA polymerase and other factors required for proper transcription. Promoters consist of several regions that are necessary for full function of the promoter. Some of these regions may be used in isolation to confer promoter activity or they may be assembled with other elements to construct new promoters. One of these regions lies immediately upstream of the coding sequence and forms a "core promoter" containing consensus sequences, typically located in a gene at about −40 to +30 base pairs (70 bp). A core promoter, which is a short DNA sequence comprised of a TATA box and other sequences that serve to specify the site of transcription initiation, to which regulatory elements may be added for control of expression. The core promoter region is often referred to as a "minimal promoter" because it is functional on its own to promote a basal level of transcription. A core promoter thus consists only of all basal elements needed for transcription initiation, e.g., a TATA box and/or an initiator. A core promoter typically has greatly reduced promoter activity in the absence of upstream activation. However, in the presence of a suitable transcription factor, the core promoter can function to permit transcription. Thus, promoters useful with the present invention may be derived in their entirety from a native gene, or may be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

In some embodiments, a core promoter may be operably linked to proximal and more distal upstream elements, the latter elements often referred to as enhancers. As used herein, an "enhancer" refers to a DNA sequence which can stimulate promoter activity and may be an innate element of the promoter or a heterologous element inserted to enhance the level or tissue specificity of a promoter. In some embodiments, an enhancer may be capable of operating in both orientations (normal or flipped), and/or may be capable of functioning even when moved either upstream or downstream from the promoter. Both enhancers and other upstream regulatory elements bind sequence-specific DNA-binding proteins that mediate their effects. Promoters may be derived in their entirety from a native gene, or may be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

A promoter useful with the present invention may be any constitutive promoter. In some embodiments, a promoter may be a tissue-specific or tissue-preferred promoter. In some embodiments, the tissue-preferred or tissue-specific promoter may be a salivary gland-specific or -preferred promoter, or a Malpighian tubule-specific or -preferred promoter. Example constitutive promoters include, but are not limited to, hsp83 and/or ubiquitin promoters. Example salivary gland-specific or -preferred promoters includes but is not limited to the promoter of the slalom gene (encodes a 3'-phosphoadenosine-phosphosulfate transporter; Ali et al. *Dev. Genes Evol.* 215:537-544 (2005)). In some embodiments, a promoter may be a core promoter or minimal promoter. Example core promoter or minimal promoters include, but are not limited to, a core promoter of an hsp70 gene from *Lucilia cuprina* and/or an hsp70, a P element and/or a Pgd gene from *Drosophila melanogaster*. As understood in the art a core promoter is typically from about −40 to about +30 bp of a gene (about 70 bp).

A nucleotide sequence encoding a signal peptide may be operably linked at the 5'- or 3'-terminus of a heterologous nucleotide sequence or nucleic acid molecule. Signal peptides (and the targeting nucleotide sequences encoding them) are well known in the art and can be found in public databases such as the "Signal Peptide Website: An Information Platform for Signal Sequences and Signal Peptides." (signalpeptide.de); the "Signal Peptide Database" (see, proline.bic.nus.edu.sg/spdb/index) (Choo et al., *BMC Bioinformatics* 6:249 (2005)); ChloroP (see, dtu.dk/services/ChloroP/; predicts the presence of chloroplast transit peptides (cTP) in protein sequences and the location of potential cTP cleavage sites); LipoP (see, cbs.dtu.dk/services/LipoP/; predicts lipoproteins and signal peptides in Gram negative bacteria); MITOPROT (see, ihg2.helmholtz-muenchen.de/ihg/mitoprot; predicts mitochondrial targeting sequences); PlasMit (see, gecco.org.chemie.uni-frankfurt.de/plasmit/index; predicts mitochondrial transit peptides in *Plasmodium falciparum*); Predotar (see, urgi.versailles.inra.fr/predotar/predotar.; predicts mitochondrial and plastid targeting sequences); PTS1 (see, mendel.imp.ac.at/mendeljsp/sat/pts1/PTS1predictor.jsp; predicts peroxisomal targeting signal 1 containing proteins); SignalP (see, cbs.dtu.dk/services/SignalP/; predicts the presence and location of signal peptide cleavage sites in amino acid sequences from different organisms: Gram-positive prokaryotes, Gram-negative prokaryotes, and eukaryotes). The SignalP method incorporates a prediction of cleavage sites and a signal peptide/non-signal peptide prediction based on a combination of several artificial neural networks and hidden Markov models; and TargetP (see, cbs.dtu.dk/services/TargetP/); predicts the subcellular location of eukaryotic proteins—the location assignment is based on the predicted presence of any of the N-terminal presequences such as secretory pathway signal peptide (SP)). Example signal peptides useful with the present invention include, but are not limited to, MKSFLL-VLFAFLAVFAFVQA (SEQ ID NO:1) or the signal peptide from the 87 amino acid venom peptide (p300) identified in *Lucilia sericata* salivary gland.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Methods
Insect Rearing and Germline Transformation

The CA06 and MD wild type strains of L. sericata were raised under similar conditions as described previously [38, 60]. To make the MDLA mixed strain, 16 MD males were mated with 30 CA06 virgin females, the offspring collected and reared to adults. For heat shock experiments, MDLA or L. sericata PD1 eggs were placed on milk, yeast, egg, agar larval media (MYEA) (50 g whole egg powder, 25 g instant non-fat milk powder, 12.5 g inactivated dry yeast, 7.5 g agar, 500 mL deionized water) at 27° C. overnight. First instar larvae were transferred to a new MYEA dish then heat shocked at 37° C. or left at 27° C. control for 3h. The larvae were collected and then washed with water using a filter, attached to an aspirator. Larvae were then snap frozen in liquid nitrogen and stored at −80° C. Introgression of the DR4 #14 line into a L. sericata genetic background was done by crossing 125 DR4 #14 L. cuprina males with 80 MDLA virgin females. Male offspring were then crossed with MDLA virgin females for two generations. The male and female offspring allowed to breed freely to establish the line.

piggyBac-mediated germ-line transformation of L. sericata was as previously described [37, 38] using a mixture of Lchsp83-pBac DNA (200 µg/mL) and in vitro synthesized piggyBac RNA helper (300 µg/mL). Homozygous Lucilia individuals were selected at the wandering third instar larval stage based on fluorescence intensity and bred to create a stable line.

Plasmid Construction

To make the pB[Lchsp24-pdgf-B] construct, firstly the Lchsp24 promoter [35] was amplified from L. cuprina genomic DNA with the primer pair 5'-GAGCTCCTCGAGTAGGGTGGGCAAT-TTTTTCTAATGCCCATTA-3' (SEQ ID NO:3) and 5'-GGATCCTGGATAGGCTTCACGGTCCAGTTCATC-GAT-3' (SEQ ID NO:4) and the fragment inserted into pBAC2 vector [37]. The Lchsp70 3' UTR and 3' flanking DNA [35] were amplified from L. cuprina genomic DNA with the primer pair 5'-AAGCTTAGTCAATCTCAATTT-CATTCC-3' (SEQ ID NO:5) and 5'-GCGGCCGCCTCGAGAATGATATATACAAGGA-3' (SEQ ID NO:6), and inserted downstream of the Lchsp24 promoter. However, the Lchsp24 promoter fragment retained the start codon, so this was removed by amplification of a portion of Lchsp24 without the start codon with the primer pair 5'-ATTATCATTATC-TACTAGTTCAGTTCTAGTTAC-3' (SEQ ID NO:7) and 5'-ATTATCGGATCCCTCTTTGGTTTTCTTAAA ACG-3' (SEQ ID NO:8), then digested with SpeI and BamHI(blunt) and inserted into SpeI and AgeI(blunt) of pB[Lchsp24-pl-Lchsp70], effectively replacing the promoter with an identical fragment minus the ATG codon. A DNA fragment was synthesized by Genscript that encoded the human PDGF-B protein and a 20 amino acid signal peptide (MKSFLLVLFAFLAVFAFVQA) (SEQ ID NO:1) from an 87 amino acid venom peptide that was expressed in *L. sericata* salivary glands [36] and detected in larval ES (P.H. Nibbering, personal communication). The nucleotide sequence was optimized for expression in *L. cuprina*. The pdgf-B Genscript plasmid was digested with flanking Asp718 (blunt) and AvrII and inserted into NheI (blunt) and AvrII of pBAC2[Lchsp24-Lchsp70]. A PspOMI and partial SpeI digest of pB[Lchsp83-ZsGreen-tub.2] [37] released a 3.3 kb Lchsp83-ZsGreen-tub.2 cassette which was inserted into PspOMI and SpeI of pBSII KS+. The resulting pBSII KS+[Lchsp83-ZsGreen-tub.2] plasmid was digested with NotI and PspOMI and inserted into NotI digested pB[Lchsp24-pdg/B-Lchsp70] to create the final piggyBac transformation vector,pB[Lchsp24-pdgf-B].

To construct DR4 and EF-PDGF, the general strategy was to first assemble the driver or effector gene cassette in the cloning vector pBluescript II KS (−) and then excise the gene cassette by digestion with XhoI and NotI and clone into the unique XhoI and PspOMI sites in the piggyBac transformation vectors pB [Lchsp83-ZsGreen] [37] or pB[Lchsp83-DsRedex2] [38]. To assemble the effector construct, an spdgf-b fragment was amplified from pB[Lchsp24-pdgf-B].using the primer pair 5'-TTATCATGAAGTCGTTCTTGTTGGTGTTG-3'(SEQ ID NO:9) and 5'-TGAAAGCTTAGGTCACGGGACGGGCGGCAG-3' (SEQ ID NO:10), digested with BspHI and HindIII, and ligated to pBS-FL11 (Li et al., 2014) that had been digested with NcoI and HindIII. The effector gene cassette was then excised from the pBS-EF-PDGF plasmid and ligated with the pB[Lchsp83-DsRedex2] transformation vector.

For 5' Rapid Amplification of cDNA Ends (RACE), total RNA was extracted from *C. hominivorax* embryos using TRI reagent (Sigma). polyA+RNA was purified by oligo-dT chromatography (Sigma). 5' RACE-ready cDNA was prepared using the SMARTer RACE cDNA amplification kit (Takara) according to the manufacturers instructions. RACE-ready cDNAs were diluted in 20 μL Tris-EDTA (TE) buffer (Clontech), and then 2 μL was used for 5' RACE with the primer 5'-CAATTCACGCAAGAAAATCTCTTTGTTGGAATAGAAGGT-3' (SEQ ID NO:11). "Genome walker" libraries were prepared from *C. hominivorax* genomic DNA using the Universal GenomeWalker kit (Takara) following the manufacturers instructions. PCR was then performed using the Chhsp83 gene specific primers (GSP) 5'-GATCAACCACAATCTAATATATTATAACTTTTTTCACTTTTCAGTT-3' (SEQ ID NO:12) and 5'-TTGTCTTTTCGCTCGCTTGGAAACTCTCGATGTAT-3' (SEQ ID NO:13). The Chhsp83 gene promoter fragment for the DR4 construct was obtained by PCR amplification with genomic DNA template using the primers 5'-ATAGCGGCCGCTGTCATTACTAGAGTTTAAGTTATAACAATTGTAT-3' (SEQ ID NO:14) and 5'-ACGCTGCAGATCTGGAAATACAATAGGAAAAATAAAGTTAGCGAATT-3' (SEQ ID NO:15), then cloned into pGEM-T (Promega). The Chhsp83 promoter fragment was excised and ligated with pBS-FL1 that had been digested with NotI and PstI, essentially replacing the tetO-Dmhsp70 enhancer-promoter with the Chhsp83 promoter. The Chhsp83-tTAv-SV40 gene cassette was then excised and ligated with the pB [Lchsp83-ZsGreen] transformation vector.

The GenBank accession numbers for the plasmids made in this study are: pB[Lchsp24-pdgf-B]: KT897708; DR4: KT897710; EF-PDGF: KT897709

Genomic DNA Isolation and Inverse PCR

Five to 6 frozen adults were ground to powder with a mortar and pestle under liquid nitrogen. Powder was dissolved in 4 mL fresh STE buffer (50 mM Tris-HCl, pH 7.5, 100 mM NaCl, 10m M EDTA, pH 8). Two hundred μL 10%

SDS and 8 μL RNase A (Cat #R4642-250MG Sigma Aldrich St. Louis, Mo.) were added and samples were incubated at 56° C. After 30 min, Proteinase K (Cat #P2308-100MG Sigma Aldrich) was added to 100 μg/mL and the sample was incubated overnight at 56° C. Three mL phenol:chloroform: isoamyl alcohol [25:24:1] (Cat #P2069, Sigma) was added and samples were rotated 10 min at 12 RPM at 22° C. Samples were then centrifuged 10 min at 1000 g at 4° C. The aqueous layer was transferred to a new tube and the extraction was repeated. One tenth volume 3M sodium acetate, pH 5.2 and 2 volumes cold 100% ethanol were added and mixed. The samples were incubated at −20° C. for 1 h and centrifuged 30 min at 7200 g at 4° C. The supernatant was removed from the pellet, which was washed with 1 mL cold 75% ethanol. The pellet was air-dried 10 min before resuspension in 50-100 μL TE Buffer. To determine genomic sequence flanking the transgene insertion, inverse PCR was performed with MboI, TaqαI, and MspI-digested genomic DNA templates as described previously [61, 38].

RT-PCR and qRT-PCR

RT-PCR was performed with cDNA template from total RNA isolated from larvae as described previously [62]. The pdgf-b primer used were PDGF-F (5'- ATG AAG TCG TIC TTG TTG GTG TTG TTC GCC TTC TTG GCC GTT-3') (SEQ ID NO:16) and PDGF-R (5'-CCG GAG TTT AAA CCC TAG GCG CGC CAT GAG CTC AAG CTT TCA TTA-3') (SEQ ID NO:17). For RNA isolation for quantitative RT-PCR (qRT-PCR), 5-6 frozen larvae were homogenized in 500 μL of Trizol (Cat #15596026 Life Technologies/Thermo Fisher Scientific Waltham, Mass.) in a 1 mL glass homogenizer that had been previously baked at 200° C. overnight. 100 μL of chloroform was added, and samples were shaken for 15 s and allowed to incubate at 22° C. for 15 min. Samples were centrifuged at 18,000 g for 15 minutes at 4° C. The aqueous layer was mixed with an equal volume cold RNase-free 70% ethanol, mixed, and loaded on a Qiagen RNeasy Mini Kit column (Cat #74104 Qiagen Venlo, Netherlands). The purification was performed according to the kit protocol, including the optional on-column DNAse digest using the RNase-free DNAse set (Cat #79254 Qiagen). A subsequent in-solution DNAse digest was performed to eliminate residual DNA, followed by a second round of column purification. cDNA was synthesized from 3.5 μg of DNAse treated RNA using Superscript III (Cat #18080-400 Invitrogen) according to manufacturer's instructions. Random hexamers were used as primers. Negative control reactions containing water instead of enzyme mix were performed to confirm the absence of DNA contamination.

PDGF qPCR primers were designed using Primer3: hPDGF F (5'-GAAATTGTGCGTAAAAAGCCCATTT) (SEQ ID NO:18) and hPDGF R (5'-AACAGTTTCACAT-TTACAGGCCAAA) (SEQ ID NO:19). Primers were tested for efficiency by creating a dilution series of cDNA. Template was pipetted into quadruplicate wells of a 384 well optical plate (Cat #4309849 Applied Biosystems). Thermo Maxima SYBR Green/Rox qPCR Master Mix 2X (Cat #K0221 Thermo Fisher Scientific Waltham, Mass.) was added to primers to create a master mix, which was dispensed into wells via a multi-channel pipet. The plate was sealed (Cat #4311971 Applied Biosystems), mixed then centrifuged 1 min at room temperature at 1600 g. The qPCR run was performed on a BioRad CFX384 C1000 Touch Thermocycler (BioRad Hercules, Calif.) using the following program: 95° C. 10 min, [95° C. 15 s, 60° C. 60 s] 40×. Data acquisition was performed on the anneal/extension step. Primer efficiency was determined by plotting the log of the starting template dilution on the X-axis and the mean quantification cycle (Cq) of the quadruplicate replicates on the Y-axis. The slope of the best fit line was used in the following equation to calculate efficiency: [Efficiency=−1+ $10^{(-1/slope)}$]. Primers were accepted if efficiency was 90-105% and re-designed if efficiency fell outside this range.

For measurement of relative transcript levels, cDNA templates were diluted 1:4 with nuclease-free water then pipetted into quadruplicate wells of a 384 well optical plate for each primer set, hPDGF and the 28s rRNA reference gene. The 28S rRNA primer pair were Lc-28SF (5'-AC-CACTGTTCACACGAAACCCTTC-3') (SEQ ID NO:20) and Lc-28SR (5'-ATCTCGGTTGGATTTTAAACTTT-GAAA-3') (SEQ ID NO:21).The qPCR protocol was performed as above. Analysis of delta delta Cq was performed using BioRad CFX Manager. Mean Cq value was found for each set of 4 replicate wells. The reference gene was utilized to calculate ΔCq. The EF-PDGF control was chosen as the calibrator sample and set to 1. The bar graph represents ΔΔCq (relative normalized expression), with error bars representing standard error of the mean for the replicate values.

Protein Analysis

With the PD1 line (Lchsp24-pdgfb), prior to hemolymph collection, adult flies were heat shocked at 37° C. for 2 h with access to water and allowed to recover at room temperature for 3 h. Flies were anesthetized by exposure to carbon dioxide and then one wing was removed. The hemolymph was squeezed into a capillary tube pre-filled with a small amount of cold hemolymph collection buffer (10 mM EDTA pH7 in 1× phosphate-buffered saline (PBS)+1× Protease inhibitor cocktail (Cat #P2714, Sigma-Aldrich, St. Louis, Mo.) on ice. Samples were centrifuged 2 min at 10,000 g at 4° C. Supernatant was transferred to a new tube. Multiple adults were pooled for one sample. Samples were stored at −80° C.

For offspring of the cross between DR4 driver and EF-PDGF effector, third instar larvae were sorted by fluorescence and rinsed with water on a vacuum funnel with gentle suction. Larvae were briefly placed on a Kim Wipe to remove excess moisture before being placed in Eppendorf tubes and snap frozen in liquid nitrogen. For ES collection, larvae were processed as above and then placed into wells of a 12-well flat-bottomed polystyrene tissue culture plate. Six or 50 larvae were added per well. Two hundred μL (for 6 larvae) or 1 mL (for 50 larvae) of ES collection buffer (Ringer Solution [0.120 mM NaCl, 1.5 mM $CaCl_2$, 5 mM KCl, pH 7.4, filter sterilized]+1× Protease inhibitor cocktail) was added per well, and wells were sealed with an adhesive plate sealer. After 40 minutes, ES was removed and centrifuged at 21,000 g for 30 min at 4° C. Supernatant was transferred to a new tube and stored at −80° C., and debris pellet was discarded. Frozen larvae were lysed on ice in cold gentle lysis buffer [63] using 1 mL glass homogenizers. Following homogenization, lysates were centrifuged at 15,000 g 15 min at 4° C. Supernatant was transferred to a new tube and stored at −80° C., while debris pellet was discarded.

Total protein concentration was determined for lysates and hemolymph using the Pierce BCA Protein Assay Kit (Cat #23227, Thermo Fisher, Rockford, Ill.) and for ES using Quickstart Bradford 1× Dye Reagent and Quickstart Bovine Gamma Globulin Standard (Cat #500-0205 and 500-0208, BioRad, Hercules, Calif.). The hPDGF-BB Quantikine ELISA kit was purchased from R&D Systems (Cat #DBB00) and assay was performed according to kit protocol. Lysate and ES samples were assayed in triplicate wells, containing 150 µg and 15-60 µs protein per well respectively. Eighty µs of total protein from each hemolymph sample was assayed per well. Recombinant His-tagged human PDGF-BB (Cat #ab73231, Abcam, Cambridge, Mass.) was assayed on each ELISA run and provided a positive, in-range control for the integrity of the kit. Sample concentrations were extrapolated or interpolated from a standard curve constructed from the log PDGF-BB concentration (pg/L) on the X-axis and the log mean optical density reading (OD) on the Y-axis. Error bars represent standard error of the mean for the replicate values.

Results

Heat Inducible Expression of PDGF-B in Transgenic L. sericata

A heat-inducible system was chosen for PDGF-B expression as it provides several advantages. If fitness costs were observed, flies could be reared in non-permissive conditions in order to obtain sufficient numbers of larvae. Further, during clinical application of larvae, the wound temperature will generate the permissive condition and induce PDGF-B expression. We previously showed that the Lucilia cuprina hsp24 (Lchsp24) gene is strongly induced by heat shock in first and third instar larvae [35]. Further, several putative heat shock factor binding sites were identified within 500 bp upstream of the transcription start site. Thus the Lchsp24 promoter was selected to make the heat inducible PDGF-B gene construct, pB[Lchsp24-pdgf-B] (FIG. 1, panel A). The Lchsp24 gene fragment contained 1016 bp upstream of the start of transcription and 180 bp of the 5' UTR. The translation start codon was not included in the fragment. A gene fragment encoding the mature active form of pdgf-b gene was synthesized with a codon usage optimal for expression in Lucilia. To facilitate secretion from L. sericata larvae, an amino terminal predicted signal peptide was included in the synthesized pdgf-b gene. The signal peptide was identified in a venom peptide that is expressed in L. sericata larval salivary glands [36]. For polyadenylation of pdgf-b transcripts, the gene construct contained the 3'UTR and 3' flanking DNA from a Lchsp70 gene. The Lchsp24-pdgf-b-pA gene construct was inserted into a piggyBac transformation vector used previously [37] (FIG. 1, panel A). The vector contains a ZsGreen marker gene under the control of a strong constitutive promoter (Lchsp83) for identification of transgenic larvae.

L. sericata CA06 embryos were injected with pB[Lchsp24-pdgf-B] DNA and a piggyBac helper DNA/RNA mixture [37, 38]. Four transgenic lines were obtained from 18 $G_0$ adults that developed from injected embryos. Two lines showed the predicted Mendelian inheritance for a single transgene (e.g. crossing heterozygotes with CA06 gave 50% fluorescent offspring). Molecular analysis (inverse PCR) also indicated that these two lines (PD1 and PD2) carried a single copy of the transgene. However, only the PD1 line was homozygous viable and fertile and so this line was selected for further analysis. The nucleotide sequence adjacent to the transgene was determined by inverse PCR (FIG. 1, panel B). The transgene had inserted into a TTAA site, which is typical for piggyBac-mediated transformation [39].

To determine if pdgf-b mRNA expression was inducible by heat shock at 37° C., RT-PCR was performed on RNA isolated from PD-1 homozygous first instar larvae. A DNA fragment of the correct size was detected from the heat-treated (37° C. for 30 min) but not control larvae (FIG. 1, panel C). This suggests that the PD-1 line provides a heat inducible system for PDGF-B expression.

Detection of PDGB-BB Protein in PD-1 Larval Lysate

We next sought to determine whether or not the human PDGF-B protein was detectable in lysates of transgenic larvae. A commercial ELISA kit was chosen due to superior sensitivity and specificity over western blot. For each assay, a positive control his-tagged recombinant human PDGF-BB was included, and yielded a positive signal within the kit standard range (data not shown). CA06 control (wt) and PD-1 larvae were subjected to a 3 h at 37° C. heat shock, then snap frozen. Lysates were normalized for total protein concentration and each sample was assayed in triplicate ELISA wells. PDGF-B was undetectable in control CA06 lysate (FIG. 2, panel A). While low basal levels of protein were detected in PD-1 larval lysate at the control temperature (27° C.), the PDGF-B protein concentration increased 5-fold with heat shock treatment (FIG. 2, panel A). For any future clinical application it is important that the PDGF-B protein is secreted from Lucilia cells and is present in larval ES. Thus we next heat-shocked larvae in ES collection buffer and collected the ES. However, PDGF-B was not detectable in larval secretions (data not shown). Total protein concentration was approximately 10-fold lower in ES samples compared to whole larval lysates. As a result, the amount of total ES protein loaded per ELISA well was one tenth to one half that of lysates. It is possible that PDGF-B was present in the ES samples but below the level of detection of the assay. We next collected protein from adult hemolymph, reasoning that the protein concentration would be higher than larval ES. PDGF-B was detected in hemolymph isolated from adult PD-1 flies after heat shock, albeit at a lower concentration than lysates (FIG. 2, panel B) These data suggest that the transgenic expression system is functional, and that PDGF-B is secreted into the hemolymph from cells in which it is expressed.

PDGF-B Expression in Transgenic L. sericata Regulated by the Tetracycline Transactivator (tTA)

Figure 3:
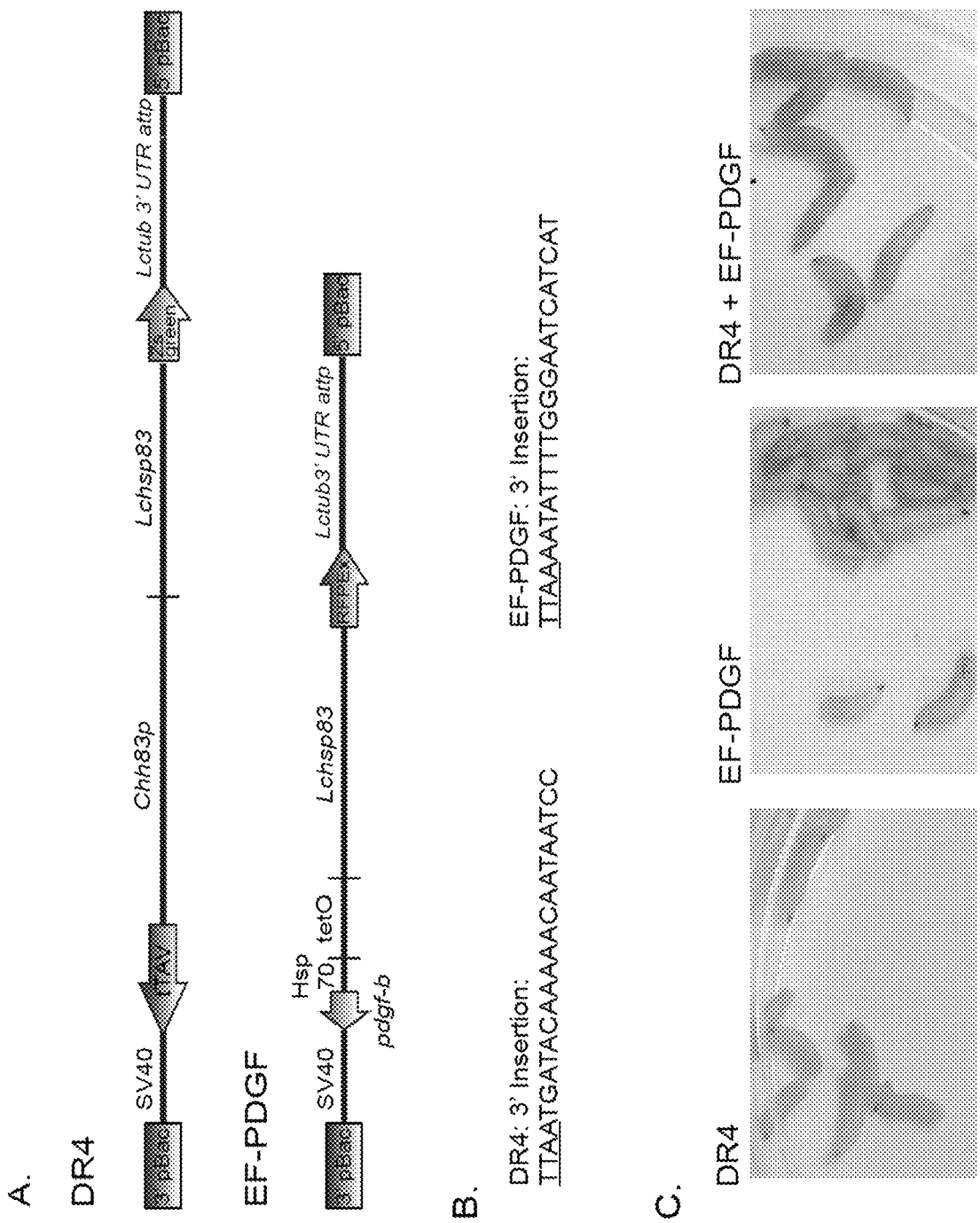
FIG. 3—tTA-mediated PDGF-B expression in transgenic *L. sericata*. A. Schematic of the DR4 tetracycline transactivator (tTA) driver and EF-PDGF tetracycline transactivator (tTA)-regulated effector gene constructs in piggyBac transformation vectors. B. Genomic DNA sequence adjacent to 3' pBac for each strain. C. DR4 #14, EF-PDGF #11, and DR4 #14+EF-PDGF #11 larvae under white light. D. Relative expression of pdgf-b mRNA in control effector alone and tTA-driver plus effector larvae. qRT-PCR analysis was performed on RNA isolated from whole larvae and normalized to the 28s rRNA reference gene.
Figure 3:
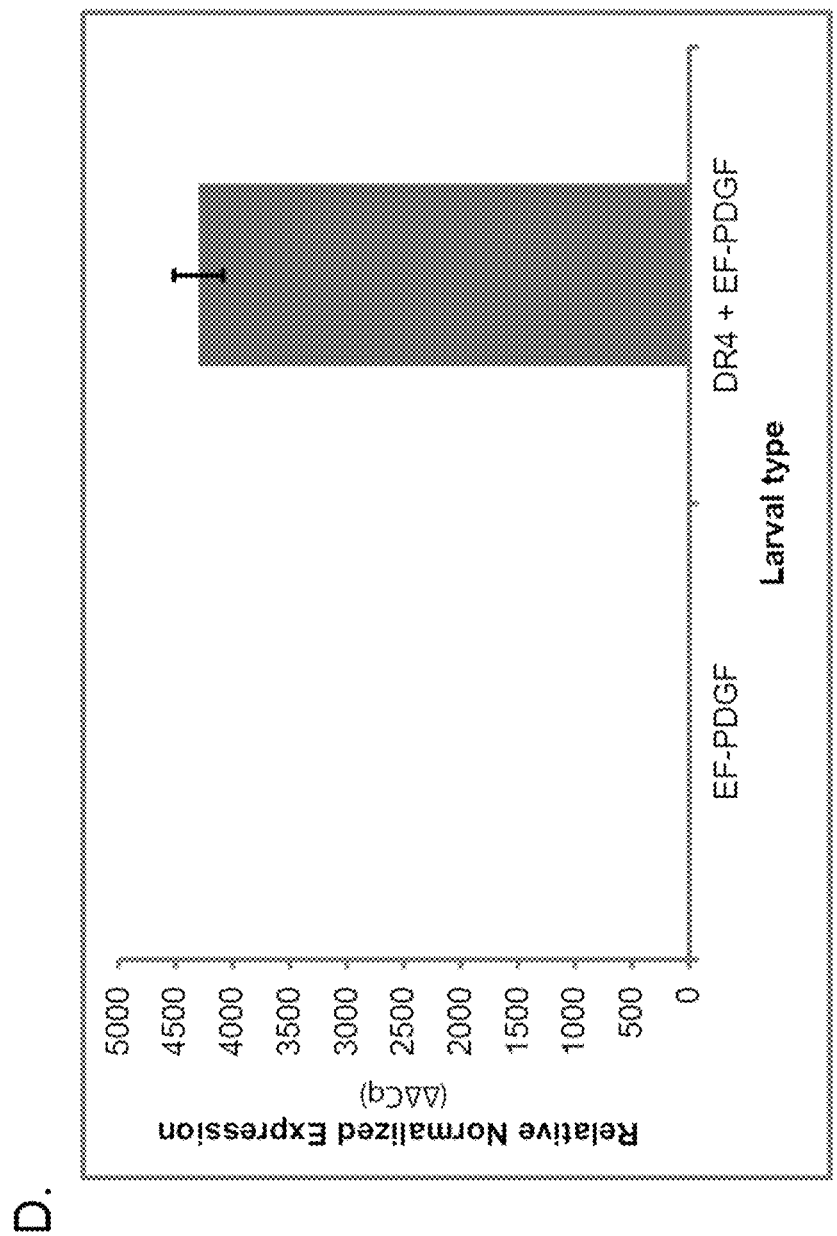

The above analysis suggested that higher levels of PDGF-B expression were needed to produce detectable levels in larval ES. The L. cuprina hsp83 promoter is a strong constitutive promoter in transgenic L. sericata [37]. Indeed, L. sericata larvae expressing DsRedex2 and ZsGreen under the control of this promoter appear light pink and greenish yellow respectively under white light (FIG. 3, panel C). We had also previously shown that the "tet-OFF" system can lead to very high levels of gene expression in transgenic Lucilia [38]. The tet-OFF system is comprised of a tTA "Driver" construct and a tTA-responsive "Effector" construct (FIG. 3, panel A). We reasoned that if the strong hsp83 promoter was used to drive tTA expression, this would lead to very high levels of the effector, which in this study would be pdgf-b. Since the L. cuprina hsp83 promoter was used for the marker gene, we isolated the hsp83 promoter from a related blowfly, Cochliomyia hominivorax (Chhsp83). The start of transcription of the Chhsp83 gene was determined by 5' RACE, using oligonucleotide primers based on a previously identified transcript [40]. The exon-intron arrangement was determined by PCR with genomic DNA template and primers based on the transcript. As for the Lchsp83 gene [35], the Chhsp83 gene contains one intron with the translation start codon at the beginning of the second exon. A PCR-based genome walking approach was used to obtain the nucleotide sequence of genomic DNA upstream from the start of transcription. The DR4 driver construct contains a 3 kb fragment from the Chhsp83 gene upstream of the tTA coding region, followed by the SV40 polyadenylation sequence. The Chhsp83 fragment includes 2225 bp of upstream flanking DNA, the 200 bp 5' UTR and the 586 bp first intron. The tTA translation start codon follows the Chhsp83 intron. The Chhsp83-tTA gene cassette was cloned in a piggyBac transformation vector with a Lchsp83-ZsGreen marker gene. The EF-PDGF effector construct includes the tetO$_{21}$-Lchsp70 enhancer-promoter upstream of the pdgf-b coding region and SV40 polyadenylation sequence. The tetO$_{21}$-Lchsp70 enhancer-promoter was used previously to achieve high levels of tTA gene expression in *L. cuprina* (autoregulated system) [38]. The pdgf-b sequence with an N-terminal signal peptide was the same as used above in the heat inducible system. The tetO-pdgf-b gene cassette was cloned into a piggyBac transformation vector with a Lchsp83-DsRedex2 marker gene.

Transgenic DR4 and EF-PDGF lines were obtained by piggyBac-mediated transformation. For DR4, 9 lines were initially obtained from 137 G$_0$. However, the lines were weak and difficult to maintain. This is mostly likely because high levels of tTA protein are toxic to *L. cuprina* [38]. Consequently, only one line, DR4 #14, was maintained and this was propagated as a mixture of heterozygotes and homozygotes. DR4 had been injected into *L. cuprina* embryos as part of the effort to make male-only lines [41]. For this study, it was necessary to introgress the DR4 transgene into a *L. sericata* genetic background. This was done by crossing *L. cuprina* DR4 #14 males with MDLA *L. sericata* females. The offspring were then backcrossed for two generations with *L. sericata* females. The *L. sericata* EF-PDGF #11 line was obtained from 32 G$_0$ and bred to homozygosity. The nucleotide sequence adjacent to the transgene insertion site was determined by inverse PCR (FIG. 3, panel B).

To induce pdgf-b expression, the DR4 #14 driver and EF-PDGF #11 effector lines were crossed and the larval offspring collected. In the presence of the antibiotic tetracycline, tTA is bound by tetracycline and rendered ineffective. In the absence of tetracycline, however, tTA is able to bind to tetO in the effector construct and activate pdgf-b expression. Third instar larvae of the driver strain express ZsGreen marker, and appear yellow green in white light, while third instar larvae of the effector strain express the DsRedex2 marker and appear light pink. The progeny of this cross with both transgenes appear bright pink (FIG. 3, panel C). This is most likely because tTA bound to tetO is also enhancing expression of the linked marker gene from the Lchsp83 gene promoter. This was previously observed in larvae that overexpress tTA [38]. To confirm induction of pdgf-b transcript, RNA was isolated and quantitative RT-PCR was performed. pdgf-b transcript was readily detected in larvae that contain one copy of each of the DR4 and EF-PDGF transgenes. Control larvae (EF-PDGF only) had very low levels of pdgf-b mRNA expression (FIG. 3, panel D). In larvae that had both transgenes there was a greater than 4000-fold increase in the level of pdgf-b RNA (FIG. 3, panel D).

PDGF-BB Protein Detection in Whole Larval Lysate and ES from Larvae Heterozygous for the DR4 tTA Driver and EF-PDGF Effector To determine if the larvae express and secrete PDGF-B, ELISA assays were performed on ES samples collected from control EF-PDGF #11 larvae and larvae with both the DR4 and EF-PDGF transgenes. As with the heat inducible system, PDGF-B was readily detected in whole larval lysate from larvae with driver and effector (FIG. 4, panel A). When the more dilute ES samples were analyzed, total protein concentration was again much less than for lysates (30-fold). Therefore, the amount of total ES protein per ELISA well was one tenth to one half that of lysates. However, PDGF-B was detected in ES samples from larvae that have both DR4 and EF-PDGF transgenes (FIG. 4, panel B). Mean PDGF-B concentration in ES was more variable between experiments than for whole larval lysates. Taken together, these data indicate that human PDGF-B is produced and secreted from third instar *L. sericata* larvae from a two-component transgene expression system.

Discussion

Proteins of human and other origins have been expressed in insect cells in culture for decades [42]. More similar to our study, human protein has also been expressed in tissue of insects using transient viral-based [43] and transgenic systems [44]. For example, Medin and colleagues reported detection of recombinant human adenosine deaminase, a primarily non-secreted protein, in *Trichoplusia ni* larval lysate after injection of a baculovirus-mediated transgene [43]. Interest in expressing heterologous proteins in insect larvae has arisen from the desire for greater scale-up capabilities than is feasible using cells in culture. A more recent study demonstrated expression of a recombinant mouse anti-botulinum antibody fragment (Fab) in *Trichoplusia ni* larvae [45]. A secretory signal from *Bombyx mori* was utilized to facilitate secretion of the protein product from larval cells, however, protein was purified from whole larvae. Lastly, secreted human proteins, including growth factors, have been expressed in *Bombyx mori* and purified from hemolymph as well as larval/pupal homogenate, and several of these proteins have proven functional in the veterinary clinic [46]. We show here for the first time that the translational and secretory mechanisms of the *L. sericata* larvae is capable of producing a human growth factor from our transgene expression systems, and that this protein is indeed detectable in hemolymph, larval lysate, and larval secretions. Further, we introduce the first human transgene expression in a larval host with potential for human clinical applications.

Two conditional systems were employed in this study, one regulated by temperature and the other by addition of tetracycline to the insect diet. The temperature-regulated system was chosen because pdgf-b expression would theoretically increase upon application of the larvae to patient. Although pdgf-b expression driven by the Lchsp24 promoter was heat-inducible in whole larvae, we failed to detect PDGF-B protein in maggot ES. The *D. melanogaster* hsp23 gene shows tissue-specificity and a cell-specific heat-shock response [47], therefore it's possible that Lchsp24 promoter has low activity in *Lucilia* larval tissues that excrete/secrete proteins found in ES. Nevertheless, our finding that the Lchsp24 promoter is active and heat inducible could be useful for conditional expression of other proteins in blow flies. Further, PDGF-B was detected in adult hemolymph after heat shock. This suggests that the pre-protein was likely correctly processed and secreted from *Lucilia* cells. Lastly, the inducible systems utilized in our study provide the possibility of "pre-treating" larvae with temperature or diet to induce expression before wound application, thereby maximizing delivery of the secreted factor and healing potential.

Using the two-component tet-OFF system, we have demonstrated that human PDGF-B can be expressed in *L. sericata* larvae and detected in ES in an efficient inducible system. Great potential exists as well, for expression of other proteins or factors utilizing our system to further increase the effectiveness of MDT by other mechanisms. Extensive study has been done demonstrating the antibacterial properties of specific fractions and factors in larval ES against panels of bacteria commonly found in wounds [48, 49].

Lucifensin is in an insect defensin previously purified from *L. sericata* larval salivary glands, fat bodies, and hemolymph shown to have antibacterial activity against Gram positive bacteria [12]. Lucifensin was also purified from ES and maggot therapy-treated wound washings, suggesting that its secretion is stimulated by the wound environment [12]. We suggest that our system could be applied to lucifensin and other small antibacterial peptides to inhibit bacterial infection in MDT patients. Antibacterial effects of ES have been tested on a large panel of bacterial species, with greater activity against Gram positive bacteria than Gram negative bacteria. Cecropins, originally identified from the giant silk moth Hyalophora cecropia [50], are small proteins (31-39aa) that interact with bacterial membranes and form ion channels. Cecropin B is particularly active against Gram negative bacteria [51], therefore cecropin B might also be an exceptional candidate for expression in larval ES using our system. The constitutively expressed DR4 tTA driver construct could be utilized with a myriad of other tTA-responsive effectors, therefore broadening the potential utility of our system, as well as making possible more tailored therapy for MDT patients, as different wounds may benefit from treatment with distinctive factors based on the species of bacteria present in an infection, stage of wound healing, and level of inflammation. Clinicians might have at their disposal a panel of larvae expressing different factors to be applied strategically to specific patients, in combination or sequentially, in order to obtain maximum benefit for each individual wound.

The DR4 driver in our system may be further improved. The DR4 driver is not the best choice for building strains intended for clinical application, as high levels of tTA expression are toxic for *Lucilia*. A tTA driver employing a larval salivary gland-specific gene promoter would be advantageous [52, 36], as confining tTA expression to one tissue would likely have a lower fitness cost for the insect. Further, any effector protein induced by tTA would be secreted from the salivary gland. The tet-OFF system could not be utilized in the clinic if tetracycline or a derivative was being used to treat an infected wound. If this proved to be problematic, the two-component GAL4-UAS system, widely used in *Drosophila* [53], could be considered for protein expression in *Lucilia*. With this system, it should be possible to achieve similar levels of protein expression as with the tet-OFF system, however expression would not be conditional.

As with any treatment modality, clinical application of genetically modified *L. sericata* would require regulatory approval. A potential challenge for the utility of modified MDT is patient attitude toward maggot application. However, several studies indicate that patients will accept MDT [54, 55]. Indeed, Steenvoorde et al., indicate that 89% of patients surveyed would undergo MDT again and 94% would recommend it to other patients [55]. Further, with the availability of polymer Biobags or pouches made of nylon or chiffon fabric [56], it may be possible to provide a liquid-permeable barrier when applying sterile genetically modified (GM) maggots to a wound, thereby making the treatment significantly more tolerable for opposing patients. It would also be anticipated that some patients would reject treatment with genetically modified maggots given the public opposition to genetically modified crops [57]. However, the genetically modified maggots could be more acceptable, as the use of a fluorescent protein marker should facilitate thorough removal of maggots from a wound after treatment. The larvae could be readily visualized using goggles equipped with the appropriate filter sets [58].

Here we show robust, inducible production of human PDGF-B protein from two conditional expression systems in transgenic *L. sericata* larvae. PDGF-B protein was detectable in hemolymph, larval lysate, and ES of these larvae following induction. Our system could be used to deliver customizable proteins and peptides to the wound environment with the aim of enhancing wound healing, thereby improving patient outcome. Further, enhancing MDT through larval secretion of beneficial growth or antibacterial factors such as PDGF-B may potentially amplify the effectiveness of MDT without a large increase in cost. The International Diabetes Federation reports that 80% of people with diabetes live in low or middle income countries [1]. Enhanced MDT may be a cost-effective solution for patients with less access to other treatment modalities.

The foregoing is illustrative of the present invention, and is not to be construed as limiting thereof. The invention is defined by the following claims, with equivalents of the claims to be included therein.

REFERENCES

1. Website for idf.org/diabetesatlas.
2. Rice J B, Desai U, Cummings A K, Birnbaum H G, Skornicki M, Parsons N B. Burden of diabetic foot ulcers for medicare and private insurers. Diabetes Care. 2014; 37(3):651-8.
3. Wayman J, Nirojogi V, Walker A, Sowinski A, Walker M A. The cost effectiveness of larval therapy in venous ulcers. J Tissue Viability. 2000; 10(3):91-4.
4. Thomas S, Jones M. Wound debridement: evaluating the costs. Nurs Stand. 2001; 15(22):59-61.
5. Chan D C, Fong D H, Leung J Y, Patil N G, Leung G K. Maggot debridement therapy in chronic wound care. Hong Kong Med J. 2007; 13(5):382-6.
6. Sherman R A, Mumcuoglu K Y, Grassberger M, Tantawi T I. Maggot Therapy. In: Grassberger M, Sherman R A, Gileva O S, Kim CMH, Mumcuoglu K Y, editors. Biotherapy—History, Principles and Practice: A Practical Guide to the Diagnosis and Treatment of Disease using Living Organisms. Dordrecht: Springer; 2013. p. 5-29.
7. Sherman R A, Hall M J, Thomas S. Medicinal maggots: an ancient remedy for some contemporary afflictions. Annu Rev Entomol. 2000; 45:55-81.
8. Jeffcoate W J, Price P, Harding K G, International Working Group on Wound H, Treatments for People with Diabetic Foot U. Wound healing and treatments for people with diabetic foot ulcers. Diabetes Metab Res Rev. 2004; 20 Suppl 1:S78-89.
9. Lerch K, Linde H J, Lehn N, Grifka J. Bacteria ingestion by blowfly larvae: an in vitro study. Dermatology. 2003; 207(4):362-6.
10. Robinson W. Ammonium bicarbonate secreted by surgical maggots stimulates healing in purulent wounds. Am J Surg. 1940; 47:111-5.
11. Cazander G, Pritchard D I, Nigam Y, Jung W, Nibbering P H. Multiple actions of *Lucilia sericata* larvae in hard-to-heal wounds: larval secretions contain molecules that accelerate wound healing, reduce chronic inflammation and inhibit bacterial infection. Bioessays. 2013; 35(12): 1083-92.
12. Cerovsky V, Zdarek J, Fucik V, Monincova L, Voburka Z, Bem R. Lucifensin, the long-sought antimicrobial factor of medicinal maggots of the blowfly *Lucilia sericata*. Cell Mol Life Sci. 2010; 67(3):455-66.
13. Andersen A S, Sandvang D, Schnorr K M, Kruse T, Neve S, Joergensen B et al. A novel approach to the antimicrobial activity of maggot debridement therapy. J Antimicrob Chemother. 2010; 65(8):1646-54.
14. Altincicek B, Vilcinskas A. Septic injury-inducible genes in medicinal maggots of the green blow fly *Lucilia sericata*. Insect Mol Biol. 2009; 18(1):119-25.
15. Huberman L, Gollop N, Mumcuoglu K Y, Block C, Galun R. Antibacterial properties of whole body extracts and haemolymph of *Lucilia sericata* maggots. J Wound Care. 2007; 16(3):123-7.
16. Kawabata T, Mitsui H, Yokota K, Ishino K, Oguma K, Sano S. Induction of antibacterial activity in larvae of the blowfly *Lucilia sericata* by an infected environment. Med Vet Entomol. 2010; 24(4):375-81.
17. Beasley W D, Hirst G. Making a meal of MRSA—the role of biosurgery in hospital-acquired infection. J Hosp Infect. 2004; 56(1):6-9.
18. van der Plas M J, van der Does A M, Baldry M, Dogterom-Ballering H C, van Gulpen C, van Dissel J T et al. Maggot excretions/secretions inhibit multiple neutrophil pro-inflammatory responses. Microbes Infect. 2007; 9(4):507-14.
19. van der Plas M J, Baldry M, van Dissel J T, Jukema G N, Nibbering P H. Maggot secretions suppress pro-inflammatory responses of human monocytes through elevation of cyclic AMP. Diabetologia. 2009; 52(9):1962-70.
20. Mumcuoglu K Y, Ingber A, Gilead L, Stessman J, Friedmann R, Schulman H et al. Maggot therapy for the treatment of intractable wounds. Int J Dermatol. 1999; 38(8):623-7.
21. Mumcuoglu K Y. Clinical applications for maggots in wound care. Am J Clin Dermatol. 2001; 2(4):219-27.
22. Honda K, Okamoto K, Mochida Y, Ishioka K, Oka M, Maesato K et al. A novel mechanism in maggot debridement therapy: protease in excretion/secretion promotes hepatocyte growth factor production. Am J Physiol Cell Physiol. 2011; 301(6):C1423-30.
23. Prete P E. Growth effects of Phaenicia *sericata* larval extracts on fibroblasts: mechanism for wound healing by maggot therapy. Life Sci. 1997; 60(8):505-10.
24. Heldin C H, Westermark B. Mechanism of action and in vivo role of platelet-derived growth factor. Physiol Rev. 1999; 79(4):1283-316.
25. Papanas N, Maltezos E. Becaplermin gel in the treatment of diabetic neuropathic foot ulcers. Clin Intery Aging. 2008; 3(2):233-40.
26. Pierce G F, Tarpley J E, Allman R M, Goode P S, Serdar C M, Morris B et al. Tissue repair processes in healing chronic pressure ulcers treated with recombinant platelet-derived growth factor B B. Am J Pathol. 1994; 145(6): 1399-410.
27. Senet P, Vicaut E, Beneton N, Debure C, Lok C, Chosidow O. Topical treatment of hypertensive leg ulcers with platelet-derived growth factor-B B: a randomized controlled trial. Arch Dermatol. 2011; 147(8):926-30.
28. Wieman T J, Smiell J M, Su Y. Efficacy and safety of a topical gel formulation of recombinant human platelet-derived growth factor-B B (becaplermin) in patients with chronic neuropathic diabetic ulcers. A phase III randomized placebo-controlled double-blind study. Diabetes Care. 1998; 21(5):822-7.
29. Smiell J M, Wieman T J, Steed D L, Perry B H, Sampson A R, Schwab B H. Efficacy and safety of becaplermin (recombinant human platelet-derived growth factor-B B) in patients with nonhealing, lower extremity diabetic ulcers: a combined analysis of four randomized studies. Wound Repair Regen. 1999; 7(5):335-46.
30. Rees R S, Robson M C, Smiell J M, Perry B H. Becaplermin gel in the treatment of pressure ulcers: a phase I I randomized, double-blind, placebo-controlled study. Wound Repair Regen. 1999; 7(3):141-7.
31. Nagai M K, Embil J M. Becaplermin: recombinant platelet derived growth factor, a new treatment for healing diabetic foot ulcers. Expert Opin Biol Ther. 2002; 2(2): 211-8.
32. Zykova S N, Jenssen T G, Berdal M, Olsen R, Myklebust R, Seljelid R. Altered cytokine and nitric oxide secretion in vitro by macrophages from diabetic type I I-like db/db mice. Diabetes. 2000; 49(9):1451-8.
33. Falanga V. Wound healing and its impairment in the diabetic foot. Lancet. 2005; 366(9498):1736-43.
34. Fang R C, Galiano R D. A review of becaplermin gel in the treatment of diabetic neuropathic foot ulcers. Biologics. 2008; 2(1):1-12.
35. Concha C, Edman R M, Belikoff E J, Schiemann A H, Carey B, Scott M J. Organization and expression of the Australian sheep blowfly (*Lucilia cuprina*) hsp23, hsp24, hsp70 and hsp83 genes. Insect Mol Biol. 2012; 21(2): 169-80.
36. Sze S H, Dunham J P, Carey B, Chang P L, Li F, Edman R M et al. A de novo transcriptome assembly of *Lucilia sericata* (Diptera: Calliphoridae) with predicted alternative splices, single nucleotide polymorphisms and transcript expression estimates. Insect Mol Biol. 2012; 21(2): 205-21.
37. Concha C, Belikoff E J, Carey B L, Li F, Schiemann A H, Scott M J. Efficient germ-line transformation of the economically important pest species *Lucilia cuprina* and *Lucilia sericata* (Diptera, Calliphoridae). Insect Biochem Mol Biol. 2011; 41(1):70-5.
38. Li F, Wantuch H A, Linger R J, Belikoff E J, Scott M J. Transgenic sexing system for genetic control of the Australian sheep blow fly *Lucilia cuprina*. Insect Biochem Mol Biol. 2014; 51:80-8.
39. Lobo N, Li X, Fraser M J, Jr. Transposition of the piggyBac element in embryos of *Drosophila melanogaster, Aedes aegypti* and *Trichoplusia ni*. Mol Gen Genet. 1999; 261(4-5):803-10.
40. Guerrero F D, Dowd S E, Djikeng A, Wiley G, Macmil S, Saldivar L et al. A database of expressed genes from *Cochliomyia hominivorax* (Diptera: Calliphoridae). J Med Entomol. 2009; 46(5):1109-16.
41. Scott M J. Development and evaluation of male-only strains of the Australian sheep blowfly, *Lucilia cuprina*. BMC Genet. 2014; 15 Suppl 2:S3.
42. van Oers M M, Pijlman G P, Vlak J M. Thirty years of baculovirus-insect cell protein expression: from dark horse to mainstream technology. J Gen Virol. 2015; 96(Pt 1):6-23.
43. Medin J A, Hunt L, Gathy K, Evans R K, Coleman M S. Efficient, low-cost protein factories: expression of human adenosine deaminase in baculovirus-infected insect larvae. Proc Natl Acad Sci USA. 1990; 87(7):2760-4.
44. Fossgreen A, Bruckner B, Czech C, Masters C L, Beyreuther K, Paro R. Transgenic *Drosophila* expressing human amyloid precursor protein show gamma-secretase activity and a blistered-wing phenotype. Proc Natl Acad Sci USA. 1998; 95(23):13703-8.
45. O'Connell K P, Kovaleva E, Campbell J H, Anderson P E, Brown S G, Davis D C et al. Production of a recombinant antibody fragment in whole insect larvae. Mol Biotechnol. 2007; 36(1):44-51.

46. Kato T, Kajikawa M, Maenaka K, Park E Y. Silkworm expression system as a platform technology in life science. Appl Microbiol Biotechnol. 2010; 85(3):459-70.
47. Michaud S, Marin R, Tanguay R M. Regulation of heat shock gene induction and expression during *Drosophila* development. Cell Mol Life Sci. 1997; 53(1):104-13.
48. Jaklic D, Lapanje A, Zupancic K, Smrke D, Gunde-Cimerman N. Selective antimicrobial activity of maggots against pathogenic bacteria. J Med Microbiol. 2008; 57(Pt 5):617-25.
49. Thomas S, Andrews A M, Hay N P, Bourgoise S. The anti-microbial activity of maggot secretions: results of a preliminary study. J Tissue Viability. 1999; 9(4):127-32.
50. Hultmark D, Steiner H, Rasmuson T, Boman H G. Insect immunity. Purification and properties of three inducible bactericidal proteins from hemolymph of immunized pupae of Hyalophora cecropia. Eur J Biochem. 1980; 106(1):7-16.
51. Moore A J, Beazley W D, Bibby M C, Devine D A. Antimicrobial activity of cecropins. J Antimicrob Chemother. 1996; 37(6):1077-89.
52. Ali R A, Mellenthin K, Fahmy K, Da Rocha S, Baumgartner S. Structural conservation of the salivary gland-specific slalom gene in the blowfly *Lucilia sericata*. Dev Genes Evol. 2005; 215(10):537-43.
53. Elliott D A, Brand A H. The GAL4 system: a versatile system for the expression of genes. Methods Mol Biol. 2008; 420:79-95.
54. Thomas S, Jones M, Wynn K, Fowler T. The current status of maggot therapy in wound healing. Br J Nurs. 2001; 10(22 Suppl):S5-8, S10, S2.
55. Steenvoorde P, Buddingh T J, van Engeland A, Oskam J. Maggot therapy and the "yuk" factor: an issue for the patient? Wound Repair Regen. 2005; 13(3):350-2.
56. Grassberger M, Fleischmann W. The biobag—a new device for the application of medicinal maggots. Dermatology. 2002; 204(4):306.
57. Blancke S, Van Breusegem F, De Jaeger G, Braeckman J, Van Montagu M. Fatal attraction: the intuitive appeal of GMO opposition. Trends Plant Sci. 2015; 20(7):414-8.
58. S B M, Gao S, Zhu N, Sudlow G P, Liang K, Som A et al. Binocular Goggle Augmented Imaging and Navigation System provides real-time fluorescence image guidance for tumor resection and sentinel lymph node mapping. Sci Rep. 2015; 5:12117.
59. Dorsett-Martin W A. Rat models of skin wound healing: a review. Wound Repair Regen. 2004; 12(6):591-9.
60. Li F, Vensko S P, 2nd, Belikoff E J, Scott M J. Conservation and Sex-Specific Splicing of the transformer Gene in the Calliphorids *Cochliomyia hominivorax, Cochliomyia macellaria* and *Lucilia sericata*. PLoS One. 2013; 8(2):e56303.
61. Li X, Heinrich J C, Scott Mk piggyBac-mediated transposition in *Drosophila melanogaster*: an evaluation of the use of constitutive promoters to control transposase gene expression. Insect Mol Biol. 2001; 10:447-55.
62. Edman R M, Linger R J, Belikoff E J, Li F, Sze S H, Tarone A M et al. Functional characterization of calliphorid cell death genes and cellularization gene promoters for controlling gene expression and cell viability in early embryos. Insect Mol Biol. 2015; 24(1):58-70.
63. Oku H, Shimizu T, Kawabata T, Nagira M, Hikita I, Ueyama A et al. Antifibrotic action of pirfenidone and prednisolone: different effects on pulmonary cytokines and growth factors in bleomycin-induced murine pulmonary fibrosis. Eur J Pharmacol. 2008; 590(1-3):400-8.

We claim:

1. A recombinant nucleic acid construct comprising, 5' to 3', an enhancer-promoter operably linked to a polynucleotide encoding a mammalian growth factor or an antimicrobial peptide and a mammalian growth factor, wherein the enhancer-promoter is functional in an insect cell and comprises an enhancer sequence comprising at least two copies of a binding site of a transcription factor operably linked to a core promoter, wherein the mammalian growth factor is a platelet derived growth factor B (PDGF-B), a fibroblast growth factor 1 (FGF1), a fibroblast growth factor 2 (FGF2), a hepatocyte growth factor (HGF), a keratinocyte growth factor (KGF), a granulocyte macrophage colony-stimulating factor (GM-CSF), and/or an epidermal growth factor (EGF).

2. The recombinant nucleic acid construct of claim 1, wherein the polynucleotide encoding a growth factor comprises a 5' and a 3' end and is operably linked at its 5' end to a polynucleotide encoding a signal peptide.

3. The recombinant nucleic acid construct of claim 2, wherein the signal peptide is MKSFLLVLFAFLAVFAFVQA (SEQ ID NO:1) or is a signal peptide from p300.

4. The recombinant nucleic acid construct of claim 1, wherein the promoter is (a) a constitutive promoter, (b) a salivary gland-specific promoter and/or a Malpighian tubule-specific promoter, or (c) a heat-inducible promoter.

5. The recombinant nucleic acid construct of claim 1, wherein the binding site comprises a tet operator (tetO) for tTA, an upstream activating sequence (UAS) for GAL4, a MphR(A)-specific operator for ET and/or a VanO operator for Van1.

6. A transgenic maggot excreting or secreting a mammalian growth factor or mammalian growth factor and an antimicrobial peptide comprising: a first recombinant nucleic acid construct and a second recombinant nucleic acid construct, wherein the first recombinant nucleic acid construct comprises, 5' to 3', a promoter operably linked to a polynucleotide encoding a transcription factor, and the second recombinant nucleic acid construct comprises, 5' to 3', an enhancer-promoter operably linked to a polynucleotide encoding a mammalian growth factor or a mammalian growth factor and an antimicrobial peptide, wherein the enhancer-promoter comprises an enhancer sequence comprising at least two copies of a binding site of the transcription factor operably linked to a promoter and the mammalian growth factor is a platelet derived growth factor B (PDGF-B), a fibroblast growth factor 1 (FGF1), a fibroblast growth factor 2 (FGF2), a hepatocyte growth factor (HGF), a keratinocyte growth factor (KGF), a granulocyte macrophage colony-stimulating factor (GM-C SF), and/or an epidermal growth factor (EGF).

7. The transgenic maggot of claim 6, wherein the promoter operably linked to a polynucleotide encoding a transcription factor is fa) a constitutive promoter, fb) a salivary gland-specific promoter and/or a Malpighian tubule-specific promoter, or (c) a heat-inducible promoter.

8. The transgenic maggot of claim 6, wherein the transcription factor is a tetracycline transactivator (tTA), a transcription activator protein GAL4, an erythromycin transactivator (ET), or a vanillic acid transactivator (Van1).

9. The transgenic maggot of claim 6, wherein the polynucleotide encoding a growth factor comprises a 5' and a 3' end and is operably linked at its 5' end to a polynucleotide encoding a signal peptide.

10. The transgenic maggot of claim 9, wherein the signal peptide is MKSFLLVLFAFLAVFAFVQA (SEQ ID NO:1) or is a signal peptide from p300.

11. The transgenic maggot of claim 6, wherein the promoter operatively linked to an enhancer sequence is (a) a constitutive promoter, (b) a salivary gland-specific promoter and/or a Malpighian tubule-specific promoter, or (c) a heat-inducible promoter.

12. The transgenic maggot of claim 6, wherein the binding site comprises a tet operator (tetO) for tTA, an upstream activating sequence (UAS) for GAL4, a MphR(A)-specific operator for ET and/or a VanO operator for Van1.

13. The transgenic maggot of claim 6, wherein the maggot is *Lucilia sericata* or Protophormia terraenovae.

14. A transgenic maggot excreting or secreting an antimicrobial peptide and/or a mammalian growth factor comprising the recombinant nucleic acid construct of claim 1.

15. A method of debriding a wound in a subject, comprising:
    applying to the wound of the subject an effective amount of transgenic maggots of claim 6.

16. A method of promoting wound healing in a subject, comprising:
    applying to the wound of the subject an effective amount of transgenic maggots of claim 6.

17. The method of claim 15, wherein the wound is a diabetic foot ulcer.

18. The recombinant nucleic acid construct of claim 1, wherein the enhancer-promoter functional in an insect cell is from a blowfly, optionally wherein the blowfly is *Lucilia sericata, Lucilia cuprina, Cochliomyia hominivorax* or *Protophormia terraenovae*.

* * * * *

UNITED STATES PATENT AND TRADEMARK OFFICE
CERTIFICATE OF CORRECTION

PATENT NO. : 11,248,237 B2
APPLICATION NO. : 15/923595
DATED : February 15, 2022
INVENTOR(S) : Scott et al.

It is certified that error appears in the above-identified patent and that said Letters Patent is hereby corrected as shown below:

In the Specification

Column 9, Line 59: Please correct "AgeI(blunt)" to read -- AgeI(blunt) --

Column 10, Line 10: Please correct "[Lchsp24-pdg/B-Lchsp70]" to read
-- [*Lchsp24-pdg*/B-*Lchsp70*] --

Column 11, Line 24: Please correct "TIC" to read -- TTC --

Column 12, Line 20: Please correct "AACq" to read -- ΔΔCq --

Column 13, Line 1: Please correct "15-60 μs" to read -- 15-60 μg --

Column 13, Line 2: Please correct "Eighty ρs" to read -- Eighty μg --

Column 17, Line 13: Please correct "Hyalophora cecropia" to read -- *Hyalophora cecropia* --

In the Claims

Column 28, Line 50, Claim 6: Please correct "(GM-C SF)" to read -- (GM-CSF) --

Column 28, Line 54, Claim 7: Please correct "fa)" to read -- (a) --

Column 28, Line 54, Claim 7: Please correct "fb)" to read -- (b) --

Column 29, Line 11, Claim 13: Please correct "Protophormia terraenovae" to read -- *Protophormia terraenovae* --

Signed and Sealed this
Seventeenth Day of May, 2022

Katherine Kelly Vidal
*Director of the United States Patent and Trademark Office*